US010695565B2

(12) United States Patent
Monteiro et al.

(10) Patent No.: US 10,695,565 B2
(45) Date of Patent: Jun. 30, 2020

(54) SYSTEM AND METHOD TO MITIGATE MOTION SICKNESS OR EMESIS IN A VEHICLE

(71) Applicant: GM GLOBAL TECHNOLOGY OPERATIONS LLC, Detroit, MI (US)

(72) Inventors: Sean S. Monteiro, Calgary (CA); David A. Canella, Pickering (CA)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 107 days.

(21) Appl. No.: 16/161,241

(22) Filed: Oct. 16, 2018

(65) Prior Publication Data

US 2020/0114150 A1 Apr. 16, 2020

(51) Int. Cl.
| | |
|---|---|
| *A61N 1/36* | (2006.01) |
| *A61B 5/00* | (2006.01) |
| *A61N 1/02* | (2006.01) |
| *A61B 5/0205* | (2006.01) |
| *G01C 21/34* | (2006.01) |
| *B60H 1/00* | (2006.01) |
| *A61F 7/00* | (2006.01) |

(Continued)

(52) U.S. Cl.
CPC ........ *A61N 1/36025* (2013.01); *A61B 5/0205* (2013.01); *A61B 5/6893* (2013.01); *A61F 7/0053* (2013.01); *A61N 1/025* (2013.01); *A61N 1/36031* (2017.08); *A61N 1/36034* (2017.08); *B60H 1/00742* (2013.01); *B60H 1/00878* (2013.01); *G01C 21/3415* (2013.01); *G01C 21/3484* (2013.01); *A61B 5/02405* (2013.01); *A61B 5/02416* (2013.01); *A61B 5/0533* (2013.01); *A61B 2562/063* (2013.01); *A61F 2007/0057* (2013.01); *A61F 2007/0093* (2013.01); *A61N 1/0472* (2013.01)

(58) Field of Classification Search
CPC .... A61N 1/3603; A61N 1/025; A61N 1/0404; A61N 1/36034; B60H 1/00878; G01C 21/3415; A61B 5/053
See application file for complete search history.

(56) References Cited

U.S. PATENT DOCUMENTS

| | | |
|---|---|---|
| 5,021,281 A | 6/1991 | Bompard et al. |
| 5,858,159 A | 1/1999 | Holbrook et al. |

(Continued)

OTHER PUBLICATIONS

Electrical Stimulation for Nausea, Vomiting and Motion Sickness (PrimaBella and ReliefBand) and Other Selected Indications, Sep. 13, 2018, pp. 1-18, Website: http://www.aetna.com/cpb/medical/data/600_699/0676.html.
International Neuromodulation Society, About Neuromodulation, Sep. 13, 2018, pp. 1-3, website: https://www.neuromodulation.com/about-neuromodulation.
Anna Lee and Lawrence TY Fan, Stimulation of the wrist acupuncture point P6 for preventing postoperative nausea and vomiting (NIH-PA Author Manuscript), Apr. 15, 2009 (published on-line), 1-64, HHS Public Access, USA (https://www.ncbi.nlm.nih.gov/pmc/articles/PMC3113464).

(Continued)

*Primary Examiner* — Carl H Layno
*Assistant Examiner* — Anh-Khoa N Dinh

(57) ABSTRACT

One general aspect includes a system to mitigate motion sickness/emesis, the system including: a memory configured to include one or more executable instructions and a processor configured to execute the executable instructions, where the executable instructions enable the processor to: in response to an activation of a motion-equalizing device installed in an interior of a vehicle, provide electric stimulus to a vehicle occupant via the motion-equalizing device, where the electric stimulus is designed to mitigate one or more symptoms of motion sickness and/or emesis for the vehicle occupant.

14 Claims, 6 Drawing Sheets

(51) Int. Cl.
*A61N 1/04* (2006.01)
*A61B 5/024* (2006.01)
*A61B 5/053* (2006.01)

(56) References Cited

U.S. PATENT DOCUMENTS

| | | | |
|---|---|---|---|
| 6,350,709 B1 | 2/2002 | Veiga | |
| 6,443,913 B1 * | 9/2002 | Kania | A61B 5/11 128/202.11 |
| 6,704,603 B1 | 3/2004 | Gesotti | |
| 6,808,587 B2 | 10/2004 | Bohm et al. | |
| 8,362,882 B2 | 1/2013 | Heubel et al. | |
| 8,550,222 B2 | 10/2013 | Browne et al. | |
| 9,521,885 B2 | 12/2016 | Weber et al. | |
| 2006/0186700 A1 | 8/2006 | Browne et al. | |
| 2006/0211934 A1 | 9/2006 | Hassonjee et al. | |
| 2008/0143080 A1 | 6/2008 | Burr | |
| 2010/0129575 A1 | 5/2010 | Veiga | |
| 2011/0062134 A1 | 3/2011 | Lochtman et al. | |
| 2012/0280479 A1 | 11/2012 | Barth et al. | |
| 2016/0089955 A1 * | 3/2016 | Ham | B60H 1/00742 165/202 |
| 2016/0303799 A1 | 10/2016 | Pettey et al. | |
| 2017/0136842 A1 * | 5/2017 | Anderson | B60G 17/016 |
| 2017/0249033 A1 | 8/2017 | Podhajny et al. | |
| 2017/0253252 A1 * | 9/2017 | Donnelly | B60W 50/0098 |
| 2017/0319844 A1 | 11/2017 | Woo et al. | |
| 2018/0344969 A1 | 12/2018 | Stoneman | |
| 2019/0192846 A1 | 6/2019 | Alexander et al. | |

OTHER PUBLICATIONS

Lee MY and Min HS, Effects of the Nei-Guan acupressure by wrist band on postoperative nausea and vomiting after middle ear surgery (PubMed.gov), Aug. 2008, 1-2, NCBI, Korea, USA (https://www.ncbi.nlm.nih.gov/pubmed/18753802).

Hewitt V and Watts R., The effectiveness of non-invasive complementary therapies in reducing postoperative nausea and vomiting following abdominal laparoscopic surgery in women: a systematic review (PubMed.gov), 2009, 1-3, NCBI, Australia, USA (https://www.ncbi.nlm.nih.gov/pubmed/27819924).

White PF, Issioui T, Jones SB, Coleman JE, Waddle JP, Markowitz SD, Coloma M, Macaluso AR, Ing CH, Comparative efficacy of acustimulation (ReliefBand) versus ondansetron (Zofran) in combination with droperidol for preventing nausea and vomiting (PubMed.gov), Nov. 2002, 1-2, NCBI, USA (https://www.ncbi.nlm.nih.gov/pubmed/12411789).

Lee A and Fan LT, Stimulation of the wrist acupuncture point P6 for preventing postoperative nausea and vomiting (PubMed.gov), Apr. 15, 2009, 1-3, NCBI, USA (https://www.ncbi.nlm.nih.gov/pubmed/19370583).

Ming JL, Kuo BI, Lin JG, Lin LC, The efficacy of acupressure to prevent nausea and vomiting in post-operative patients (PubMed.gov), Aug. 2002, 1-2, NCBI, Taiwan, USA (https://www.ncbi.nlm.nih.gov/pubmed/12139646).

Lee A and Fan LT, Table 1: Estimated NNT for preventing PONV (P6 acupoint stimulation versus sham), Apr. 15, 2009 (published on-line), 1-64, HHS Public Access, USA (https://www.ncbi.nlm.nih.gov/pmc/articles/PMC3113464).

* cited by examiner

SYSTEM AND METHOD TO MITIGATE MOTION SICKNESS OR EMESIS IN A VEHICLE

INTRODUCTION

Motion sickness is the feeling a vehicle occupant gets when the motion they sense with their inner ear is different than the motion they are visualizing. Five to ten percent of travelers are extremely sensitive to motion sickness and are unable to travel in traditional vehicles. As the adoption of autonomous vehicles and rideshare systems increase, this number of travelers unable to use the autonomous rideshare vehicles is bound to grow even larger. It is therefore desirable to provide a system and method that can mitigate vehicle occupants' nausea from motion sickness so that they are more liberated in their traveling options. Furthermore, other desirable features and characteristics of the present invention will become apparent from the subsequent detailed description of the invention and the appended claims, taken in conjunction with the accompanying drawings and this background of the invention.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system to mitigate motion sickness/emesis, the system including: a memory configured to include one or more executable instructions and a processor configured to execute the executable instructions, where the executable instructions enable the processor to: in response to an activation of a motion-equalizing device installed in an interior of a vehicle, provide electric stimulus to a vehicle occupant via the motion-equalizing device, where the electric stimulus is designed to mitigate one or more symptoms of motion sickness and/or emesis for the vehicle occupant. Other embodiments of this aspect include corresponding computer systems, apparatus, and computer programs recorded on one or more computer storage devices, each configured to perform the actions of the methods.

Implementations may include one or more of the following features. The system further including: receive general identifier information from a mobile computing device via a short-range wireless connection; based on the general identifier information, retrieve a pulsation profile; based on the pulsation profile, provide the electric stimulus to the vehicle occupant at a customized strength. The system further including, based on feedback from the vehicle occupant, adjust a strength of the electric stimulus. The system further including, in response to the activation of the motion-equalizing device, reduce an air temperature in at least a portion of the vehicle interior. The system further including, in response to the activation of the motion-equalizing device, cause a web mapping service application to offer one or more alternative vehicle routes based on motion sickness/emesis data. The system further including, in response to the activation of the motion-equalizing device, monitor the heart rate of the vehicle occupant for a duration of time via the motion-equalizing device. The system further including: if the monitored heart rate is determined to be increasing, monitor the physiological arousal of the vehicle occupant; and if both the monitored heart rate and monitored physiological arousal are determined to be increasing over a time period, increase a strength of the electric stimulus. The system where the motion-equalizing device is incorporated into a grip of a door handle of the vehicle and activation of the motion-equalizing device includes a capacitive touch connection. Implementations of the described techniques may include hardware, a method or process, or computer software on a computer-accessible medium.

One general aspect includes a vehicle including a telematics unit, the telematics unit configured to, in response to an activation of a motion-equalizing device installed in an interior of the vehicle, provide electric stimulus to a vehicle occupant via the motion-equalizing device, where the electric stimulus is designed to mitigate one or more symptoms of motion sickness and/or emesis for the vehicle occupant. Other embodiments of this aspect include corresponding computer systems, apparatus, and computer programs recorded on one or more computer storage devices, each configured to perform the actions of the methods.

Implementations may include one or more of the following features. The vehicle where the telematics unit is further configured to: receive general identifier information from a mobile computing device via a short-range wireless connection. The vehicle may also include based on the general identifier information, retrieve a pulsation profile. The vehicle may also include based on the pulsation profile, provide the electric stimulus to the vehicle occupant at a customized strength. The vehicle where the telematics unit is further configured to, based on feedback from the vehicle occupant, adjust a strength of the electric stimulus. The vehicle where the telematics unit is further configured to, in response to the activation of the motion-equalizing device, reduce an air temperature in at least a portion of the vehicle interior. The vehicle where the telematics unit is further configured to, in response to the activation of the motion-equalizing device, cause a web mapping service application to offer one or more alternative vehicle routes based on motion sickness/emesis data. The vehicle where the telematics unit is further configured to, in response to the activation of the motion-equalizing device, monitor the heart rate of the vehicle occupant for a duration of time via the motion-equalizing device. The vehicle where the telematics unit is further configured to: if the monitored heart rate is determined to be increasing, monitor the physiological arousal of the vehicle occupant; and if both the monitored heart rate and monitored physiological arousal are determined to be increasing over a time period, increase a strength of the electric stimulus. The vehicle where the motion-equalizing device is incorporated into a grip of a door handle of the vehicle and activation of the motion-equalizing device includes a capacitive touch connection. Implementations of the described techniques may include hardware, a method or process, or computer software on a computer-accessible medium.

One general aspect includes a method to mitigate motion sickness/emesis, the method including: in response to an activation of a motion-equalizing device installed in an interior of a vehicle, via a processor, providing electric stimulus to a vehicle occupant via the motion-equalizing device, where the electric stimulus is designed to mitigate one or more symptoms of motion sickness and/or emesis for the vehicle occupant. Other embodiments of this aspect include corresponding computer systems, apparatus, and computer programs recorded on one or more computer storage devices, each configured to perform the actions of the methods.

Implementations may include one or more of the following features. The method further including: receiving, via the processor, general identifier information from a mobile computing device via a short-range wireless connection; based on the general identifier information, via the processor, retrieving a pulsation profile; and based on the pulsation profile, via the processor, providing the electric stimulus to the vehicle occupant at a customized strength. The method further including, based on feedback from the vehicle occupant, via the processor, adjusting a strength of the electric stimulus. The method where the motion-equalizing device is incorporated into a grip of a door handle of the vehicle and activation of the motion-equalizing device includes a capacitive touch connection. Implementations of the described techniques may include hardware, a method or process, or computer software on a computer-accessible medium.

The above features and advantages and other features and advantages of the present teachings are readily apparent from the following detailed description for carrying out the teachings when taken in connection with the accompanying drawings.

BRIEF DESCRIPTION OF THE DRAWINGS

The disclosed examples will hereinafter be described in conjunction with the following drawing figures, wherein like numerals denote like elements, and wherein.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present system and/or method. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
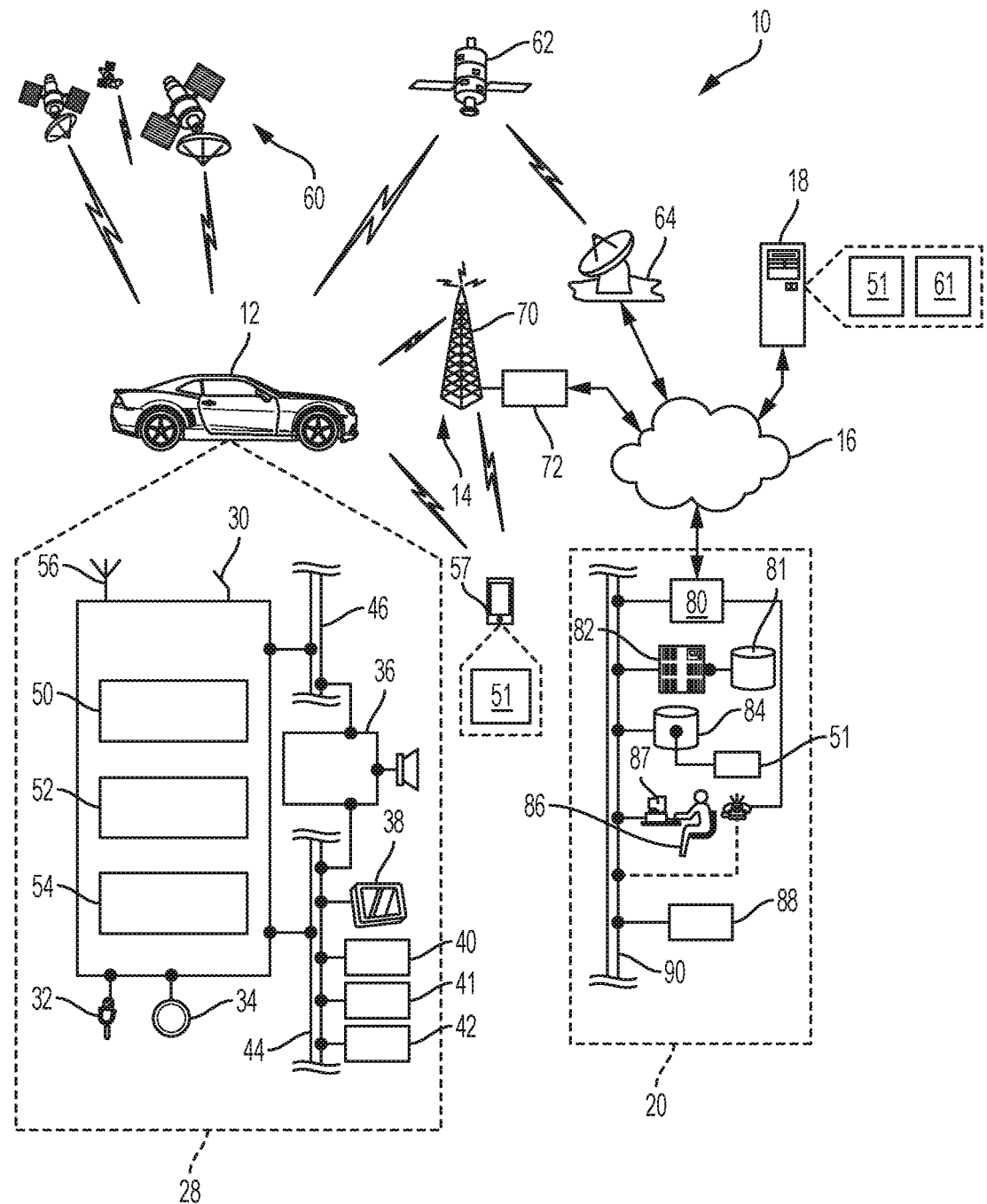
FIG. 1 is a block diagram depicting an exemplary embodiment of a communications system that is capable of utilizing the system and method disclosed herein.

With reference to FIG. 1, there is shown an operating environment that includes, among other features, a mobile vehicle communications system 10 and that can be used to implement the method disclosed herein. Communications system 10 generally includes a vehicle 12, one or more wireless carrier systems 14, a land communications network 16, a computer 18, and a data center 20. It should be understood that the disclosed method can be used with any number of different systems and is not specifically limited to the operating environment shown here. Also, the architecture, construction, setup, and operation of the system 10 and its individual components are generally known in the art. Thus, the following paragraphs simply provide a brief overview of one such communications system 10; however, other systems not shown here could employ the disclosed method as well.

Vehicle 12 is depicted in the illustrated embodiment as a passenger car, but it should be appreciated that any other vehicle including, but not limited to, motorcycles, trucks, busses, sports utility vehicles (SUVs), recreational vehicles (RVs), construction vehicles (e.g., bulldozers), trains, trolleys, marine vessels (e.g., boats), aircraft, helicopters, amusement park vehicles, farm equipment, golf carts, trams, etc., can also be used. Vehicle 12 may also be an autonomous vehicle incorporated into a rideshare or vehicle share system. Some of the vehicle electronics 28 is shown generally in FIG. 1 and includes a telematics unit 30, a microphone 32, one or more pushbuttons or other control inputs 34, an audio system 36, a visual display 38, a GPS module 40, and a motion-equalizing device 41, as well as a number of vehicle system modules (VSMs) 42. Some of these devices can be connected directly to the telematics unit 30 such as, for example, the microphone 32 and pushbutton(s) 34, whereas others are indirectly connected using one or more network connections, such as a communications bus 44 or an entertainment bus 46. Examples of suitable network connections include a controller area network (CAN), WIFI, Bluetooth and Bluetooth Low Energy, a media oriented system transfer (MOST), a local interconnection network (LIN), a local area network (LAN), and other appropriate connections such as Ethernet or others that conform with known ISO, SAE and IEEE standards and specifications, to name but a few.

Telematics unit 30 can be an OEM-installed (embedded) or aftermarket transceiver device that is installed in the vehicle and that enables wireless voice and/or data communication over wireless carrier system 14 and via wireless networking. This enables the vehicle to communicate with data center 20, other telematics-enabled vehicles, or some other entity or device. The telematics unit 30 preferably uses radio transmissions to establish a communications channel (a voice channel and/or a data channel) with wireless carrier system 14 so that voice and/or data transmissions can be sent and received over the channel. By providing both voice and data communication, telematics unit 30 enables the vehicle to offer a number of different services including those related to navigation, telephony, emergency assistance, diagnostics, infotainment, etc. Data can be sent either via a data connection, such as via packet data transmission over a data channel, or via a voice channel using techniques known in the art. For combined services that involve both voice communication (e.g., with a live advisor 86 or voice response unit at the data center 20) and data communication (e.g., to provide GPS location data or vehicle diagnostic data to the data center 20), the system can utilize a single call over a voice channel and switch as needed between voice and data transmission over the voice channel, and this can be done using techniques known to those skilled in the art.

According to one embodiment, telematics unit 30 utilizes cellular communication according to standards such as LTE or 5G and thus includes a standard cellular chipset 50 for voice communications like hands-free calling, a wireless modem for data transmission (i.e., transceiver), an electronic processing device 52, at least one digital memory device 54, and an antenna system 56. It should be appreciated that the modem can either be implemented through software that is stored in the telematics unit and is executed by processor 52, or it can be a separate hardware component located internal or external to telematics unit 30. The modem can operate using any number of different standards or protocols such as, but not limited to, WCDMA, LTE, and 5G. Wireless networking between vehicle 12 and other networked devices can also be carried out using telematics unit 30. For this purpose, telematics unit 30 can be configured to communicate wirelessly according to one or more wireless protocols, such as any of the IEEE 802.11 protocols, WiMAX, or Bluetooth. When used for packet-switched data communication such as TCP/IP, the telematics unit can be configured with a static IP address or can set up to automatically receive an assigned IP address from another device on the network such as a router or from a network address server.

Telematics unit 30 may additionally have a personalized pulsation profile 51 resident on digital memory device 54. This pulsation profile 51 includes stimulus information that can cause the M-E device 41 to deliver electric stimulus at a customized strength deemed to work best for mitigating the user's motion sickness and emesis (i.e., a stimulus having a desired pulse magnitude). The pulsation profile 51 may be stored to memory device 54 as feedback provided by the M-E device 41 or some other device (e.g., a mobile computing device 57 or heart-rate monitor). The pulsation profile 51 may also be transferred to telematics unit 30 from data center 20 or the mobile computing device 57.

The mobile computing device 57 can communicate with the telematics unit 30 and can be, for example, a smart phone, personal laptop computer, smart wearable device, or tablet computer having two-way communication capabilities, a netbook computer, or any suitable combinations thereof. The mobile computing device 57 can include memory and computer processing capability, a transceiver capable of communicating with wireless carrier system 14, and/or a GPS module capable of receiving GPS satellite signals and generating GPS coordinates based on those signals. Examples of the mobile computing device 57 include the iPhone™ manufactured by Apple, Inc. and the Pixel™ manufactured by HTC, Inc. as well as others. While the mobile computing device 57 may include the ability to communicate via cellular communications using the wireless carrier system 14, this is not always the case. For instance, Apple manufactures devices such as the various models of the iPad™ and iPod Touch™ that include the processing capability and the ability to communicate over a short-range wireless communication link such as, but not limited to, WIFI and Bluetooth. However, the iPod Touch™ and some iPads™ do not have cellular communication capabilities. Even so, these and other similar devices may be used or considered a type of wireless device, such as the mobile computing device 57, for the purposes of the method described herein.

Mobile device 57 may be used inside or outside of vehicle 12, and may be coupled to the vehicle by wire or wirelessly. The mobile device also may be configured to provide services according to a subscription agreement with a third-party facility or wireless/telephone service provider. It should be appreciated that various service providers may utilize the wireless carrier system 14 and that the service provider of the telematics unit 30 may not necessarily be the same as the service provider of the mobile devices 57.

When using a short-range wireless connection (SRWC) protocol (e.g., Bluetooth/Bluetooth Low Energy or Wi-Fi), mobile computing device 57 and telematics unit 30 may pair/link one with another when within a wireless range (e.g., prior to experiencing a disconnection from the wireless network). In order to pair, mobile computing device 57 and telematics unit 30 may act in a BEACON or DISCOVERABLE MODE having a general identification; SRWC pairing is known to skilled artisans. The general identifier may include, e.g., the device's name, unique identifier (e.g., serial number), class, available services, and other suitable technical information. Mobile computing device 57 and telematics unit 30 may also pair via a non-beacon mode. In these instances, the call center 20 may participate in pairing mobile computing device 57 and telematics unit 30. For example, the call center 20 may initiate the inquiry procedure between the telematics unit 30 and mobile computing device 57. And call center 20 may identify mobile computing device 57 as belonging to the user of vehicle 12 and then receive from the mobile computing device 57 it's unique mobile device identifier and authorize the telematics unit 30 via the wireless communication system 14 to pair with this particular ID.

Once SRWC is established, the devices may be considered bonded as will be appreciated by skilled artisans (i.e., they may recognize one another and/or connect automatically when they are in a predetermined proximity or range of one other. In other words—they may become, at least temporarily, network participants). Call center 20 may also authorize SRWC on an individual basis before completion.

The mobile computing device 57 may additionally have the personalized pulsation profile 51 resident on its memory. The pulsation profile 51 may be downloaded and stored on the device's electronic memory as part of a corresponding software application or as independent information or the pulsation profile 51 may be entered into the mobile computing device 57 by a user via one or more prompts on the device's user interface. The pulsation profile 51 may also be transferred to the mobile computing device 57 from the telematics unit 30 for storage purposes and based on feedback from the M-E device 41. As stated above, the pulsation profile 51 includes stimulus information that can cause the M-E device 41 to deliver electric stimulus at a customized strength deemed optimal for mitigating the user's motion sickness and emesis (discussed below).

Telematics Controller 52 (processor) can be any type of device capable of processing electronic instructions including microprocessors, microcontrollers, host processors, controllers, vehicle communication processors, and application specific integrated circuits (ASICs). It can be a dedicated processor used only for telematics unit 30 or can be shared with other vehicle systems. Telematics Controller 52 executes various types of digitally-stored instructions, such as software or firmware programs stored in memory 54, which enable the telematics unit to provide a wide variety of services. For instance, controller 52 can execute programs or process data to carry out at least a part of the method discussed herein.

Telematics unit 30 can be used to provide a diverse range of vehicle services that involve wireless communication to and/or from the vehicle. Such services include: turn-by-turn directions and other navigation-related services that are provided in conjunction with the GPS-based vehicle navigation module 40; airbag deployment notification and other emergency or roadside assistance-related services provided in connection with one or more vehicle system modules 42 (VSM); diagnostic reporting using one or more diagnostic modules; and infotainment-related services where music, webpages, movies, television programs, videogames and/or other information is downloaded by an infotainment module (not shown) and is stored for current or later playback. The above-listed services are by no means an exhaustive list of all of the capabilities of telematics unit 30, but are simply an enumeration of some of the services that the telematics unit 30 is capable of offering. Furthermore, it should be understood that at least some of the aforementioned modules could be implemented in the form of software instructions saved internal or external to telematics unit 30, they could be hardware components located internal or external to telematics unit 30, or they could be integrated and/or shared with each other or with other systems located throughout the vehicle, to cite but a few possibilities. In the event that the modules are implemented as VSMs 42 located external to telematics unit 30, they could utilize vehicle bus 44 to exchange data and commands with the telematics unit.

GPS module 40 receives radio signals from a constellation 60 of GPS satellites. From these signals, the module 40 can determine vehicle position that is used for providing navigation and other position-related services to the vehicle driver. Navigation information can be presented on the display 38 (or other display within the vehicle) or can be presented verbally such as is done when supplying turn-by-turn navigation. The navigation services can be provided using a dedicated in-vehicle navigation module (which can be part of GPS module 40), or some or all navigation services can be done via telematics unit 30, wherein the position information is sent to a remote location for purposes of providing the vehicle with navigation maps, map annotations (points of interest, restaurants, etc.), route calculations, and the like. The position information can be supplied to data center 20 or other remote computer system, such as computer 18, for other purposes, such as fleet management. Also, new or updated map data can be downloaded to the GPS module 40 from the data center 20 via the telematics unit 30.

Figure 2:
FIG. 2 represents an ulnar nerve and median nerve of a vehicle occupant which can be electrically stimulated in accordance with one or more exemplary embodiments.

The motion-equalizing device 41 (otherwise known as an M-E device 41) is a neuromodulation device that can be incorporated into a grip located on a handle of a vehicle door 47 (FIG. 4), or the M-E device 41 can also be incorporated into a neck cushion or arm rest of a vehicle seat. The M-E device 41 cancels or at least mitigates the symptoms of motion sickness and emesis for a vehicle occupant/user (e.g., from staring at a stationary object while vehicle 12 is moving). Moreover, capitalizing on neuromodulation, the M-E device 41 pulses an electric stimulus that desensitizes visual-vestibular miscommunications occurring in the user's body/brain. For example, when a user begins to feel nausea, the user can grip the M-E device 41 embedded into the handle grip and a capacitive touch connection will activate the M-E device 41. In response to this capacitive touch activation, the M-E device 41 can stimulate the user's ulnar nerve 100 and median nerve 102 (FIG. 2) in order to diminish the symptoms of motion sickness (i.e., stimulation of these nerves 100, 102 and their associated branches will translate into stimulation of the area postrema of the brain). Skilled artists will understand that neuromodulation technology has been well known to deliver electrical agents to the brain to produce natural biological responses such as treating neurological disorders like motion sickness.

Figure 4:
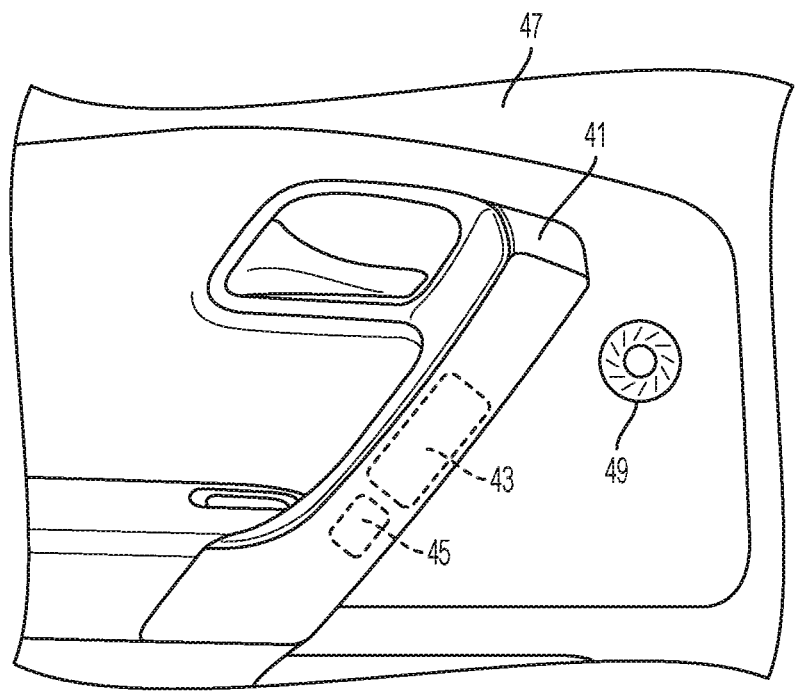
FIG. 4 depicts an exemplary aspect of the system and method disclosed herein in accordance with one or more exemplary embodiments.

The M-E device 41 can also incorporate a heart-rate monitoring (HRM) sensor 43 (FIG. 4) and a galvanic skin response (GSR) sensor 45 (FIG. 4). The HRM sensor 43 can measure heart rate measuring changes in blood flow by shining a light (e.g., from an LED) through the skin and measuring how the light scatters off blood vessels. The GSR sensor 45 measures the user's physiological arousal via the electrical conductance of their skin. Both the HRM sensor 43 and GSR sensor 45 are well known.

Apart from the audio system 36 GPS module 40, and M-E device 41, the vehicle 12 can include other VSMs 42 in the form of electronic hardware components that are located throughout the vehicle 12 and typically receive input from one or more sensors and use the sensed input to perform diagnostic, monitoring, control, reporting and/or other functions. Each of the VSMs 42 is preferably connected by communications bus 44 to the other VSMs, as well as to the telematics unit 30, and can be programmed to run vehicle system and subsystem diagnostic tests.

As examples, one VSM 42 can be an engine control module (ECM) that controls various aspects of engine operation such as fuel ignition and ignition timing, another VSM 42 can be a powertrain control module that regulates operation of one or more components of the vehicle powertrain, and another VSM 42 can be a body control module (BCM) that governs various electrical components located throughout the vehicle, like the vehicle's power door locks, air conditioning, and headlights. According to one embodiment, the engine control module is equipped with on-board diagnostic (OBD) features that provide myriad real-time data, such as that received from various sensors including vehicle emissions sensors, and provide a standardized series of diagnostic trouble codes (DTCs) that allow a technician to rapidly identify and remedy malfunctions within the vehicle. As is appreciated by those skilled in the art, the above-mentioned VSMs are only examples of some of the modules that may be used in vehicle 12, as numerous others are also possible.

Vehicle electronics 28 also includes a number of vehicle user interfaces that provide vehicle occupants with a means of providing and/or receiving information, including microphone 32, pushbuttons(s) 34, audio system 36, and visual display 38. As used herein, the term 'vehicle user interface' broadly includes any suitable form of electronic device, including both hardware and software components, which is located on the vehicle and enables a vehicle user to communicate with or through a component of the vehicle. Microphone 32 provides audio input to the telematics unit to enable the driver or other occupant to provide voice commands and carry out hands-free calling via the wireless carrier system 14. For this purpose, it can be connected to an on-board automated voice processing unit utilizing human-machine interface (HMI) technology known in the art.

The pushbutton(s) 34 allow manual user input into the telematics unit 30 to initiate wireless telephone calls and provide other data, response, or control input. Separate pushbuttons can be used for initiating emergency calls versus regular service assistance calls to the data center 20. Audio system 36 provides audio output to a vehicle occupant and can be a dedicated, stand-alone system or part of the primary vehicle audio system. According to the particular embodiment shown here, audio system 36 is operatively coupled to both vehicle bus 44 and entertainment bus 46 and can provide AM, FM, media streaming services (e.g., PANDORA RADIO™, SPOTIFY™, etc.), satellite radio, CD, DVD, and other multimedia functionality. This functionality can be provided in conjunction with or independent of the infotainment module described above. Visual display 38 is preferably a graphics display, such as a touch screen on the instrument panel or a heads-up display reflected off of the windshield, and can be used to provide a multitude of input and output functions (i.e., capable of GUI implementation). Audio system 36 may also generate at least one audio notification to announce such third-party contact information is being exhibited on display 38 and/or may generate an audio notification which independently announces the third-party contact information. Various other vehicle user interfaces can also be utilized, as the interfaces of FIG. 1 are only an example of one particular implementation.

Wireless carrier system 14 is preferably a cellular telephone system that includes a plurality of cell towers 70 (only one shown), one or more cellular network infrastructures (CNI) 72, as well as any other networking components required to connect wireless carrier system 14 with land network 16. Each cell tower 70 includes sending and receiving antennas and a base station, with the base stations from different cell towers being connected to the CNI 72 either directly or via intermediary equipment such as a base station controller. Cellular system 14 can implement any suitable communications technology, including for example, analog technologies such as AMPS, or the newer digital technologies such as, but not limited to, 4G LTE and 5G. As will be appreciated by skilled artisans, various cell tower/base station/CNI arrangements are possible and could be used with wireless system 14. For instance, the base station and cell tower could be co-located at the same site or they could be remotely located from one another, each base station could be responsible for a single cell tower or a single base station could service various cell towers, and various base stations could be coupled to a single MSC, to name but a few of the possible arrangements.

Apart from using wireless carrier system 14, a different wireless carrier system in the form of satellite communication can be used to provide uni-directional or bi-directional communication with the vehicle. This can be done using one or more communication satellites 62 and an uplink transmitting station 64. Uni-directional communication can be, for example, satellite radio services, wherein programming content (news, music, etc.) is received by transmitting station 64, packaged for upload, and then sent to the satellite 62, which broadcasts the programming to subscribers. Bi-directional communication can be, for example, satellite telephony services using satellite 62 to relay telephone communications between the vehicle 12 and station 64. If used, this satellite telephony can be utilized either in addition to or in lieu of wireless carrier system 14.

Land network 16 may be a conventional land-based telecommunications network that is connected to one or more landline telephones and connects wireless carrier system 14 to data center 20. For example, land network 16 may include a public switched telephone network (PSTN) such as that used to provide hardwired telephony, packet-switched data communications, and the Internet infrastructure (i.e., a network of interconnected computing device nodes). One or more segments of land network 16 could be implemented through the use of a standard wired network, a fiber or other optical network, a cable network, power lines, other wireless networks such as wireless local area networks (WLANs), or networks providing broadband wireless access (BWA), or any combination thereof. Furthermore, data center 20 need not be connected via land network 16, but could include wireless telephony equipment so that it can communicate directly with a wireless network, such as wireless carrier system 14.

Computer 18 can be one of a number of computers accessible via a private or public network such as the Internet. Each such computer 18 can be used for one or more purposes, such as a web server accessible by the vehicle via telematics unit 30 and wireless carrier 14. Other such accessible computers 18 can be, for example: a service center computer (e.g., a SIP Presence server) where diagnostic information and other vehicle data can be uploaded from the vehicle via the telematics unit 30; a client computer used by the vehicle owner or other subscriber for such purposes as accessing or receiving vehicle data or to setting up or configuring subscriber preferences or controlling vehicle functions; or a third party repository to or from which vehicle data or other information is provided, whether by communicating with the vehicle 12 or data center 20, or both. Computer 18 can, for example, store a web mapping service application 61 (e.g., GOOGLE MAPS™, APPLE MAPS™, etc.) that offers route planning and navigation services based on motion sickness data collected by numerous vehicles. For example, mapping application 61 may provide interactive virtual map data to telematics unit 30 to be exhibited on display 38. The interactive map data may moreover provide vehicle routes deemed to be an optimal means of travelling between two or more given locations. These vehicle routes moreover may be generated from activation and vehicle information collected from a population of vehicles 12 having M-E devices 41 installed therein. A computer 18 can also be used for providing Internet connectivity such as DNS services or as a network address server that uses DHCP or other suitable protocol to assign an IP address to the vehicle 12.

Data center 20 is designed to provide the vehicle electronics 28 with a number of different system backend functions and, according to the exemplary embodiment shown here, generally includes one or more switches 80, servers 82, databases 84, live advisors 86, as well as an automated voice response system (VRS) 88, all of which are known in the art. These various data center components are preferably coupled to one another via a wired or wireless local area network 90. Switch 80, which can be a private branch exchange (PBX) switch, routes incoming signals so that voice transmissions are usually sent to either the live advisor 86 by regular phone, backend computer 87, or to the automated voice response system 88 using VoIP. Server 82 can incorporate a data controller 81 which essentially controls the operations of server 82. Server 82 may control data information as well as act as a transceiver to send and/or receive the data information (i.e., data transmissions) from one or more of the databases 84, telematics unit 30, and mobile computing device 57.

Controller 81 is capable of reading executable instructions stored in a non-transitory machine readable medium and may include one or more from among a processor, a microprocessor, a central processing unit (CPU), a graphics processor, Application Specific Integrated Circuits (ASICs), Field-Programmable Gate Arrays (FPGAs), state machines, and a combination of hardware, software and firmware components. The live advisor phone can also use VoIP as indicated by the broken line in FIG. 1. VoIP and other data communication through the switch 80 is implemented via a modem (i.e., a transceiver), connected between the land communications network 16 and local area network 90.

Data transmissions are passed via the modem to server 82 and/or database 84. Database 84 can store account information such as vehicle dynamics information and other pertinent subscriber information. An example of pertinent subscriber information is the personalized pulsation profile 51 transmitted from mobile computing device 57 or telematics unit 30. Storing the pulsation profile 51 at the backend will allow the profile to be transferred to any vehicle 12 when requested. Data transmissions may also be conducted by wireless systems, such as 802.11x, GPRS, and the like. Although the illustrated embodiment has been described as it would be used in conjunction with a manned data center 20 using live advisor 86, it will be appreciated that the data center can instead utilize VRS 88 as an automated advisor or, a combination of VRS 88 and the live advisor 86 can be used.

METHOD

Figure 3:
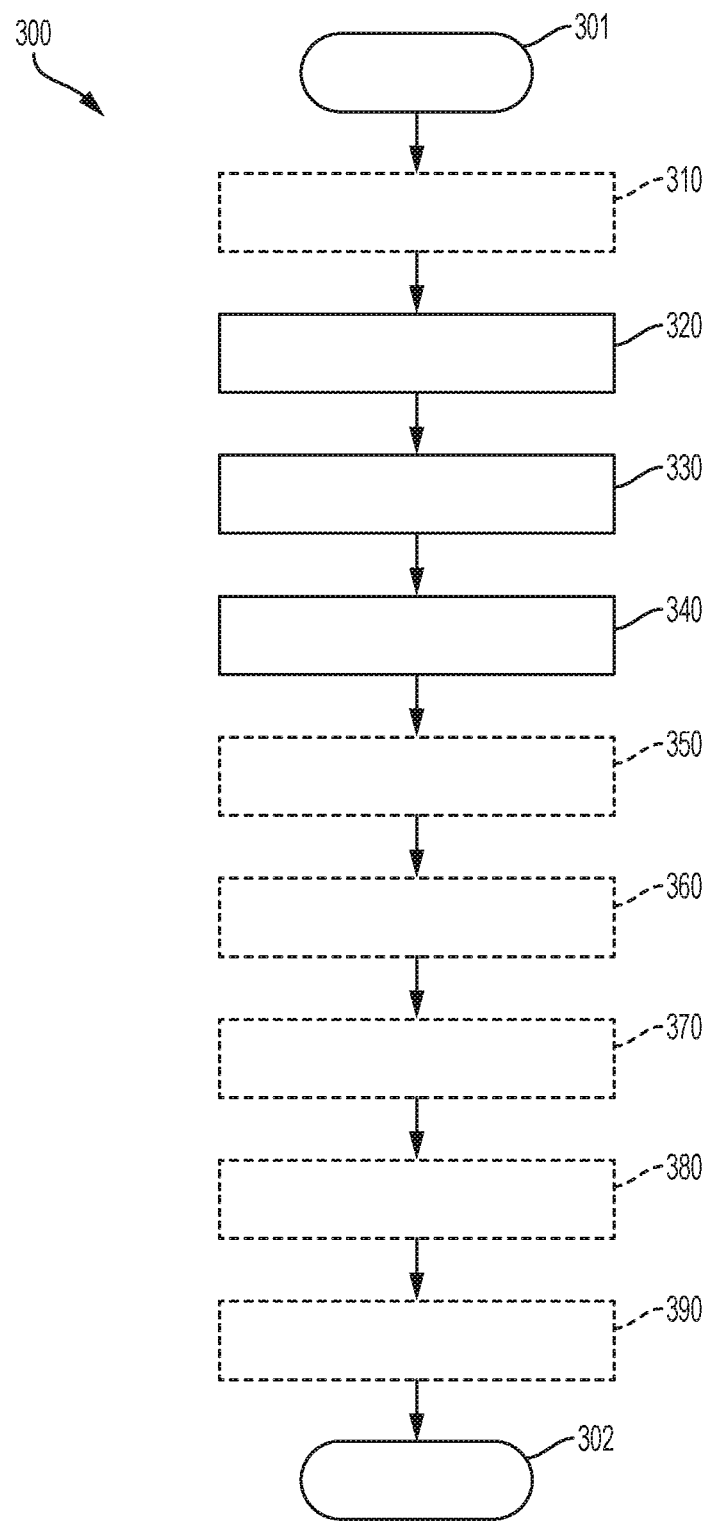
FIG. 3 is a flowchart of an exemplary process to mitigate motion sickness/emesis in accordance with one or more exemplary embodiments.

Now turning to FIG. 3, there is shown an embodiment of a method 300 to mitigate the motion sickness of a vehicle occupant. One or more aspects of the motion sickness mitigation method 300 may be completed through telematics unit 30 which may include one or more executable instructions incorporated into digital memory device 54 and carried out by electronic processing device 52. One or more ancillary aspects of method 300 may also be completed by M-E device 41, mobile computing device 57, BCM 42, data center 20, computer 18, and visual display 38. Skilled artisans will moreover see that telematics unit 30, data center 20, computer 18, and mobile computing device 57 may be remotely located from each other.

Method 300 is supported by telematics unit 30 being configured to communicate with computer 18 and data center 20. This configuration may be made by a vehicle manufacturer at or around the time of the telematics unit's assembly or after-market (e.g., via vehicle download using the afore-described communication system 10 or at a time of vehicle service, just to name a couple of examples). Method 300 is further supported by preconfiguring data center 20 to receive and store motion sickness mitigation data at databases 84. Method 300 is further supported by preconfiguring computer 18 to store the mapping application 61, which can be accessible via telematics unit 30 and/or server 82.

Method 300 begins at 301 in which a vehicle occupant enters the vehicle cabin and prepares for a ride in vehicle 12. The vehicle ignition is also turned to the ON state (i.e., starting the vehicle ignition in order to operate the vehicle). In optional step 310, when the vehicle occupant has a mobile computing device 57 on their person or has placed the device 57 somewhere in the vehicle cabin, the telematics unit 30 will pair/link with that mobile computing device 57 via a SRWC protocol (discussed above). While pairing/linking, the mobile computing device 57 will provide its general identifier information to telematics unit 30 (e.g., the device's unique identifier). In one example, after receiving the general identifier information, the telematics unit 30 will retrieve the personalized pulsation profile 51 associated with the general identifier information from one of its databases within memory device 54. In an alternative example, after receiving the general identifier information from the mobile computing device 57, the telematics unit 30 will communicate with data center 20 to retrieve the personalized pulsation profile stored in databases 84 and associated with the general identifier information. The telematics unit 30 will then store, at least temporarily, the retrieved personalized pulsation profile to digital memory device 54. In another alternative example, once properly paired/linked with mobile computing device 57, the telematics unit 30 will retrieve the personalized pulsation profile 51 directly from mobile computing device 57.

In step 320, the vehicle 12 begins travelling from the location at which the vehicle occupant entered the vehicle to some other remote location. While traveling, the vehicle occupant begins to feel nauseous as a symptom of having motion sickness or emesis. With additional reference to FIG. 4, to relieve themselves of these unwanted feelings, the vehicle occupant will grip the M-E device 41 on the handle of door 47. This gripping action, in step 330, activates the M-E device 41 via a capacitive touch connection between the vehicle occupant's hand and M-E device 41. In one or more embodiments (i.e., capacitive sensing), the M-E device 41 may include a hand outline recessed in the handle to assist in the vehicle occupant's usage of the device.

In step 340, the M-E device 41 will transmit an electric stimulus for Transcutaneous Electrical Nerve Stimulation (TENS) via one or more device embedded electrodes. In those instances when a personalized pulsation profile has been retrieved by telematics unit 30, the electric stimulus will be at a specific occupant-desired strength (current magnitude), which is associated with the mobile computing device 57 (i.e., the vehicle occupant); otherwise, the strength of the stimulus will be at some default strength (e.g., having an amplitude of 2 mA). As such, pulsations will be received by the tips of the ulnar nerve 100 and median nerve 102 (FIG. 2) in the vehicle occupant's hand. Stimulation pulsation information will then travel through the nerves 100, 102 to the appropriate cranial nerve endings on the occupant's spine and these signals will ultimately be dispersed to the area postrema of their brain, so as to mitigate their motion sickness symptoms. Moreover, as the vehicle occupant maintains their grip on the M-E device 41, their motion sickness/nausea symptoms should subside and they will have the opportunity to indulge in other tasks with their free hand. Skilled artisans will see that the position and geometry of the M-E device 41 can give the device comprehensive access to the vehicle occupant's acupressure points and stimulation points to properly stimulate the nerves 100, 102. Other embodiments of the M-E device 41 may include the device being embedded in a neck cushion on a vehicle seat and would stimulate the areas of the vehicle occupant's ulnar nerve 100 and median nerve 102 located in their neck.

Figure 5:
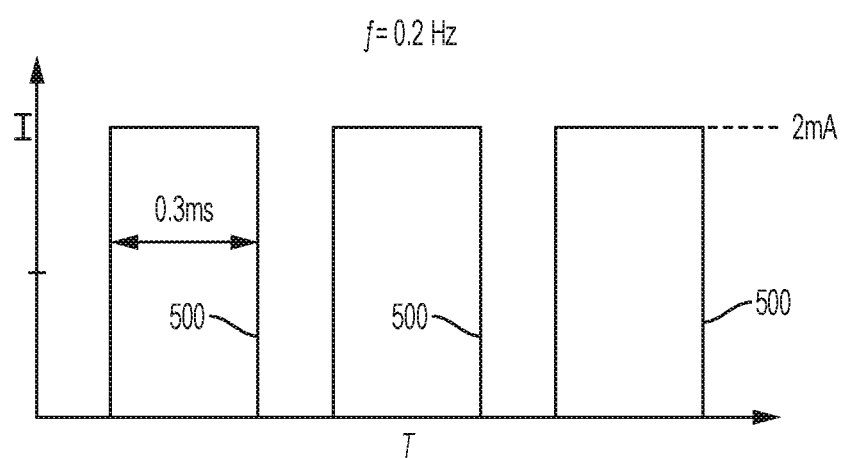
FIG. 5 depicts an application of the exemplary aspect of FIG. 4 in accordance with one or more exemplary embodiments.

An embodiment of an appropriate wave length and pulsation frequencies of the electric stimulus 500 can be seen with additional reference to FIG. 5. In this embodiment, the electric stimulus is shown as current being a function of time. The stimulus 500 has a current with a peak amplitude of two milliamps (2 mA), which can be considered a default strength, frequency of 0.2 hertz (0.2 Hz), and pulse wave width of 0.3 milliseconds (0.3 ms). It has also been found that pulses shorter than ten milliseconds (10 ms) causes contraction in the interstitial cells of Cajal (ICC). Skilled artisans should also see that an electrical stimulus at a frequency of twenty hertz (20 Hz) may also be used to mitigate motion sickness/emesis symptoms as well.

Optionally, with reference back to FIG. 4, the vehicle occupant can adjust the strength of electric stimulus by adjusting a dial 49 that is located in proximity to the M-E device 41 (e.g., four (4) inches). Adjusting the dial 49 will provide feedback to the M-E device 41 that will correspondingly increase or decrease the strength of the electric stimulus (i.e. increase/decrease the magnitude of the current of the electric stimulus). For example, someone larger than the average occupant may desire an electrical stimulus with pulses of 2.5-3 milliamps (as opposed to 2 milliamps) to mitigate their feelings of nausea. Alternatively, someone substantially smaller than the average vehicle occupant may desire a stimulus at 1 milliamp pulses to help reduce their queasiness. The vehicle occupant may also adjust the strength of the electric stimulus when they cannot make full contact with the M-E device 41 (e.g., due to fabric or hair between the device and the occupant's skin). Skilled artisans will see that the strength of the electric stimulus may be adjusted by means other than a dial such as, for example, buttons or switches.

Optionally, in step 350, to facilitate the reduction of the vehicle occupant's motion sickness/emesis symptoms, telematics unit 30 may collaborate with the BCM 42 to reduce the air temperature around the vehicle occupant by blowing cooled air at them or near them via the vehicle's HVAC system. Reducing the air temperature in the vehicle interior in this manner can help the vehicle occupant to feel better and may additionally help them to breath easier. In optional step 360, the telematics unit 30 will monitor the heart rate of the vehicle occupant via the HRM sensor 43. Monitoring the vehicle occupant's heart rate for some duration of time will help the telematics unit 30 discern the severity of the motion sickness/emesis symptoms. Monitoring the heart rate in this manner will also allow telematics unit 30 to take additional measures if/when the occupant's heart rate continues to rise (discussed below).

In optional step 370, when the vehicle occupant is using navigation services, telematics unit 30 will communicate with the web mapping service application 61 and request updated vehicle routes based on motion sickness/emesis. These vehicle routes may be based on mapping data that is a compilation of M-E device 41 activation locations, stimulus strengths, and vehicle velocities that have been provided from a population of vehicles 12 with an incorporated M-E device 41. Alternatively, activation location data and vehicle velocity data (i.e., accelerometer data) may be collected and provided from one or more mobile computing devices 57 embodied as smart phones within the population of vehicles. Moreover, when mobile computing device 57 is embodied as a smart wearable device having biometric sensors, the activation location, stimulus strength, and vehicle velocity data may be collected and provided from one or more of the wearable devices within the vehicle population.

These vehicle routes may be additionally/alternatively based on feedback data provided by a population of mobile computing devices 57. For example, when a user of mobile computing device 57 is traveling in their vehicle 12 and they begin to feel sick, they may provide feedback via the device's user interface, which is then collected by web mapping service application 61. The device's user interface may moreover provide binary feedback via one or more virtual buttons or severity data via one or more virtual sliding switches. Mobile device location information, which corresponds with the vehicle location, may also be provided with this feedback data. Alternatively/additionally, these vehicle routes may be similarly based on feedback data provided by hard-wired buttons and/or slider switch installed in a population of vehicles 12.

Figure 6:
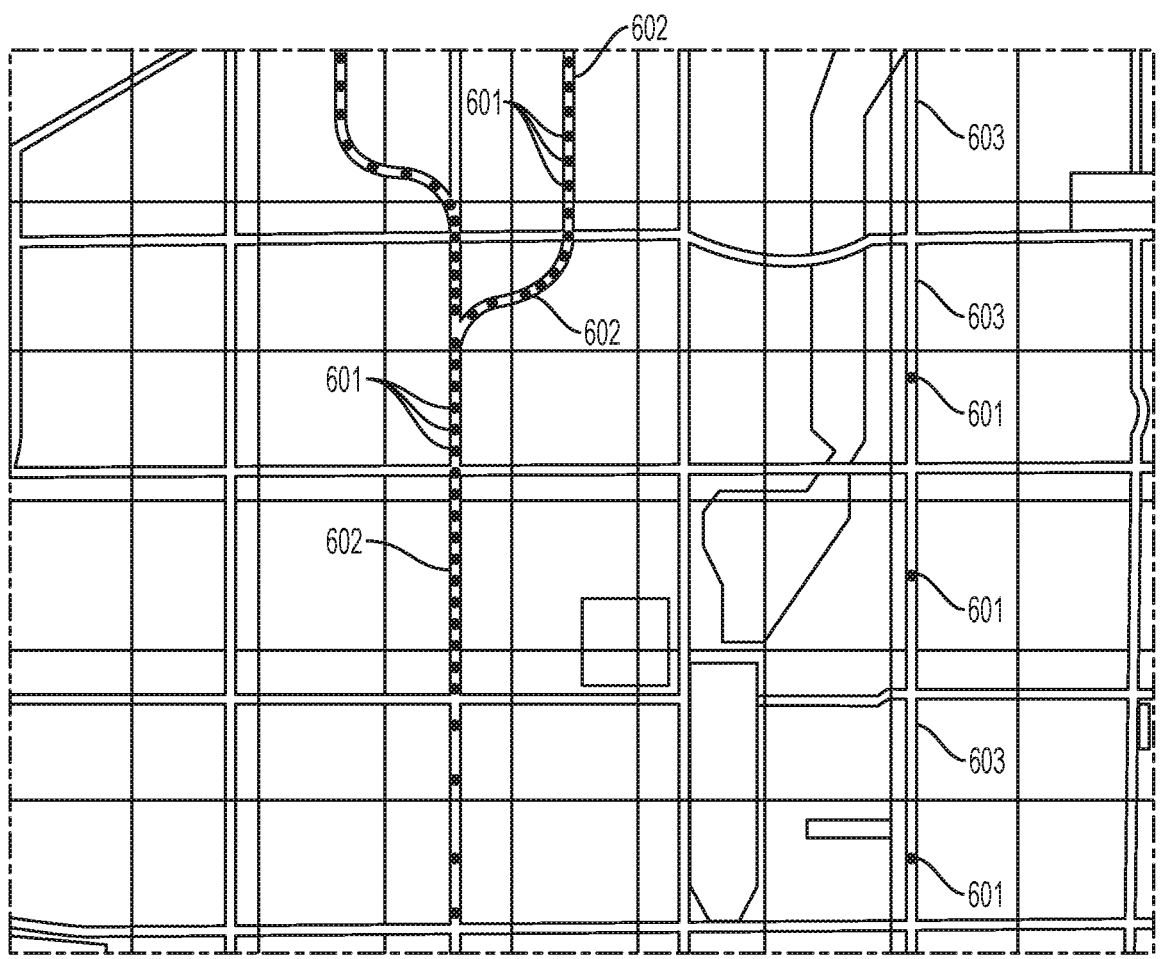
FIG. 6 depicts an exemplary aspect of the system and method disclosed herein in accordance with one or more exemplary embodiments.

With additional reference to FIG. 6, for instance, when a certain number of vehicles and/or mobile computing devices 57 transmit electric stimulus activation data at various locations 601 along a route 602, these data points may be used to deem that the route 602 is likely to induce motion sickness/emesis. However, when a relatively low number or below average number of vehicles/mobile computing devices 57 transmit electric stimulus activation data at locations 601 along another route 603, these data points may be used to consider this route 603 to be relatively unlikely to induce motion sickness. Vehicle velocity data from the vehicles/mobile computing devices 57 that have transmitted stimulus activation data may also be taken into account for these vehicle routes. For example, the stimulus activation location data may only be recorded if the velocity of the vehicle is above/below a certain vehicle speed. This also goes for stimulus strength and the duration of time the M-E device 41 remains in operation. For example, the stimulus activation location data may only be recorded if the electric stimulus is above a certain strength or if the M-E device 41 has been operational for at least a certain duration of time. Mapping application 61 may attain this M-E device usage and various vehicle data from data center 20 and analyze and compile the data to generate vehicle routes at computer 18. Mapping application 61 may also transmit the motion sickness/emesis based vehicle routes to vehicle 12 in a format that allows the routes to be exhibited via visual display 38.

In optional step 380, telematics unit 30 will log electric stimulus data (e.g., stimulus strength, duration of operation time, etc.) and store it on digital memory device 54. Telematics unit 30 may also store the vehicle location that was logged when the M-E device 41 had been activated as well as the velocity at which the vehicle was traveling when the activation occurred. To facilitate habitual use of the M-E device 41, telematics unit 30 may store at least the stimulus data to the vehicle occupant's personalized pulsation profile or, alternatively, telematics unit 30 may transfer the stimulus data to mobile computing device 57 to be stored as part of the vehicle occupant's personalized pulsation profile.

In optional step 390, telematics unit 30 will transmit the logged information to data center 20 so that data center 20 can store the information to databases 84. In those embodiments in which the pulsation profile is stored at the backend, to facilitate habitual use of the M-E device 41, data center 20 may then store at least the stimulus data to the vehicle occupant's personalized pulsation profile. Data center 20 may also organize the data in a way that it will facilitate mapping application 61 in compiling the data with that of stimulation data from a population of other vehicles 12 so as to generate one or more motion sickness/emesis based vehicle routes. After step 390, method 300 moves to completion 302.

Figure 7:
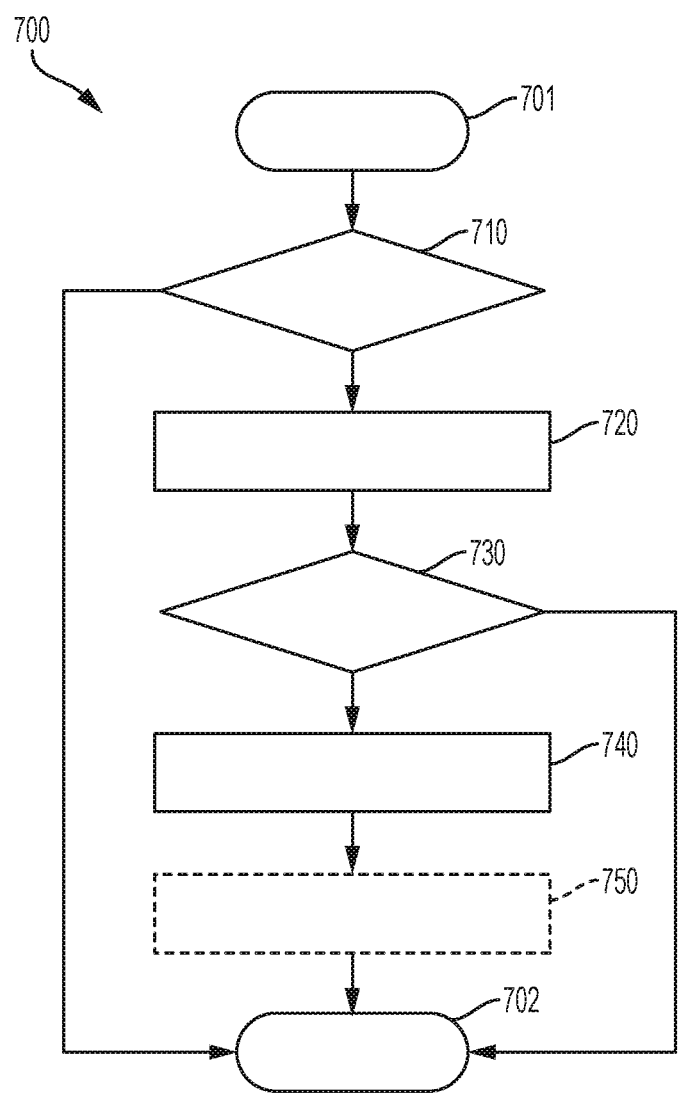
FIG. 7 is a flowchart of an exemplary additional aspect of the process of FIG. 3 in accordance with one or more exemplary embodiments.

Now turning to FIG. 7, there is shown an embodiment of a method 700 that shows the additional measures taken by telematics unit 30 if/when the occupant's heart rate is found to continue to rise after some duration of time (e.g., ten (10) minutes). Method 700 begins at 701, when the HRM sensor 43 begins monitoring the vehicle occupant's heart rate (optional step 360 of method 300, above). In step 710, over a duration of time, telematics unit 30 will determine if the vehicle occupant's heart rate has been rising. If the heart rate has been rising, method 700 will move to step 720; otherwise, since the heartrate has remained steady or has declined, method 700 will move to completion 702.

In step 720, since the heartrate has been determined to rise, telematics unit 30 will activate the GSR sensor 45 embedded in M-E device 41 to monitor the vehicle occupant's physiological arousal over another follow-on duration of time (e.g., 10 min). The telematics unit 30 will also cause HRM sensor 43 to continue monitoring the occupant's heart rate over this second duration of time (e.g., 10 min). In step 730, telematics unit 30 will determine if both of the occupant's heart rate and physiological arousal rates have been rising over the second duration of time. If both the occupant's heart rate and physiological arousal rate have been rising, then method 700 will move to step 740; otherwise, method 700 will move to completion 702 since it is unlikely the occupant's motion sickness/emesis symptoms are getting substantially worse.

In step 740, telematics unit 30 will automatically increase the strength of the electric stimulus being provided by M-E device 41. For example, telematics unit 30 may increase the stimulus strength from 2 milliamps to 4 milliamps to mitigate the occupant's symptoms. In optional step 750, to facilitate the reduction of the vehicle occupant's motion sickness/emesis symptoms, telematics unit 30 may collaborate with the BCM 42 to reduce the air temperature around the vehicle occupant by blowing cooled air at them or near them via the vehicle's HVAC system. It should be understood that telematics unit 30 may be further increasing the air conditioning around the vehicle occupant if telematics unit 30 already began reducing the air temperature around the occupant when the M-E device 41 was originally activated (step 350, discussed above). After step 750, method 700 will move to completion.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the system and/or method that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and can be desirable for particular applications.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

None of the elements recited in the claims are intended to be a means-plus-function element within the meaning of 35 U.S.C. § 112(f) unless an element is expressly recited using the phrase "means for," or in the case of a method claim using the phrases "operation for" or "step for" in the claim.

What is claimed is:

1. A system to mitigate motion sickness/emesis, the system comprising:
   a memory configured to comprise one or more executable instructions and a processor configured to execute the executable instructions, wherein the memory and processor are located in a telematics unit of a vehicle, wherein the executable instructions enable the processor to:
   pair the telematics unit with a mobile computing device via a short-range wireless connection, wherein the mobile computing device is a smart phone;
   receive general identifier information from the mobile computing device via the short-range wireless connection, wherein the general identifier information comprises a unique identifier of the mobile computing device;
   retrieve a pulsation profile associated with the unique identifier from the mobile computing device via the short-range wireless connection, wherein the pulsation profile comprises stimulus information configured to cause a motion-equalizing device to deliver electric stimulus at a customized strength, wherein the customized strength is established by a vehicle occupant;
   in response to an activation of the motion-equalizing device installed in an interior of the vehicle, provide electric stimulus to the vehicle occupant via the motion-equalizing device, wherein the electric stimulus is designed to mitigate one or more symptoms of motion sickness and/or emesis for the vehicle occupant, wherein the motion-equalizing device is incorporated into a grip of a door handle of the vehicle, wherein activation of the motion-equalizing device comprises a capacitive touch connection between a hand of the vehicle occupant and the motion-equalizing device, wherein the motion-equalizing device comprises a heart rate monitoring sensor and a galvanic skin response sensor positioned on the grip, wherein the heart rate monitoring sensor is configured to measure changes in the vehicle occupant's blood flow via light being scattered off blood vessels of the vehicle occupant; and
   based on the pulsation profile, provide the electric stimulus to the vehicle occupant at the customized strength.

2. The system of claim 1, further comprising, based on feedback from the vehicle occupant, adjust a strength of the electric stimulus.

3. The system of claim 1, further comprising, in response to the activation of the motion-equalizing device, reduce an air temperature in at least a portion of the vehicle interior.

4. The system of claim 1, further comprising, in response to the activation of the motion-equalizing device, cause a web mapping service application to offer one or more alternative vehicle routes based at least in part on motion sickness/emesis data.

5. The system of claim 1, further comprising, in response to the activation of the motion-equalizing device, monitor the heart rate of the vehicle occupant, via the heart rate monitoring sensor, for a duration of time via the motion-equalizing device.

6. The system of claim 5, further comprising:
if the monitored heart rate is determined to be increasing, monitor the physiological arousal of the vehicle occupant; and
if both the monitored heart rate and monitored physiological arousal are determined to be increasing over a time period, increase a strength of the electric stimulus.

7. A vehicle comprising a telematics unit, the telematics unit configured to:
pair with a mobile computing device via a short-range wireless connection, wherein the mobile computing device is a smart phone;
receive general identifier information from the mobile computing device via the short-range wireless connection, wherein the general identifier information comprises a unique identifier of the mobile computing device;
retrieve a pulsation profile associated with the unique identifier from the mobile computing device via the short-range wireless connection, wherein the pulsation profile comprises stimulus information configured to cause a motion-equalizing device to deliver electric stimulus at a customized strength, wherein the customized strength will be established by a vehicle occupant;
in response to an activation of the motion-equalizing device installed in an interior of the vehicle, provide electric stimulus to the vehicle occupant via the motion-equalizing device, wherein the electric stimulus is designed to mitigate one or more symptoms of motion sickness and/or emesis for the vehicle occupant, wherein the motion-equalizing device is incorporated into a grip of a door handle of the vehicle, wherein activation of the motion-equalizing device comprises a capacitive touch connection between a hand of the vehicle occupant and the motion-equalizing device, wherein the motion-equalizing device comprises a heart rate monitoring sensor and a galvanic skin response sensor positioned on the grip, wherein the heart rate monitoring sensor is configured to measure changes in the vehicle occupant's blood flow via light being scattered off blood vessels of the vehicle occupant; and
based on the pulsation profile, provide the electric stimulus to the vehicle occupant at the customized strength.

8. The vehicle of claim 7, wherein the telematics unit is further configured to, based on feedback from the vehicle occupant, adjust a strength of the electric stimulus.

9. The vehicle of claim 7, wherein the telematics unit is further configured to, in response to the activation of the motion-equalizing device, reduce an air temperature in at least a portion of the vehicle interior.

10. The vehicle of claim 7, wherein the telematics unit is further configured to, in response to the activation of the motion-equalizing device, cause a web mapping service application to offer one or more alternative vehicle routes based at least in part on motion sickness/emesis data.

11. The vehicle of claim 7, wherein the telematics unit is further configured to, in response to the activation of the motion-equalizing device, monitor the heart rate of the vehicle occupant, via the heart rate monitoring sensor, for a duration of time via the motion-equalizing device.

12. The vehicle of claim 11, wherein the telematics unit is further configured to:
if the monitored heart rate is determined to be increasing, monitor the physiological arousal of the vehicle occupant; and
if both the monitored heart rate and monitored physiological arousal are determined to be increasing over a time period, increase a strength of the electric stimulus.

13. A method to mitigate motion sickness/emesis, the method comprising:
pairing, via a processor, a telematics unit with a mobile computing device via a short-range wireless connection, wherein the mobile computing device is a smart phone;
receiving, via the processor, general identifier information from the mobile computing device via the short-range wireless connection, wherein the general identifier information comprises a unique identifier of the mobile computing device;
retrieving, via the processor, a pulsation profile associated with the unique identifier from the mobile computing device via the short-range wireless connection, wherein the pulsation profile comprises stimulus information configured to cause a motion-equalizing device to deliver electric stimulus at a customized strength, wherein the customized strength is established by a vehicle occupant;
in response to an activation of the motion-equalizing device installed in an interior of a vehicle, via a processor, providing electric stimulus to the vehicle occupant via the motion-equalizing device, wherein the electric stimulus is designed to mitigate one or more symptoms of motion sickness and/or emesis for the vehicle occupant, wherein the motion-equalizing device is incorporated into a grip of a door handle of the vehicle, wherein activation of the motion-equalizing device comprises a capacitive touch connection between a hand of the vehicle occupant and the motion-equalizing device, wherein the motion-equalizing device comprises a heart rate monitoring sensor and a galvanic skin response sensor positioned on the grip, wherein the heart rate monitoring sensor is configured to measure changes in the vehicle occupant's blood flow via light being scattered off blood vessels of the vehicle occupant; and
based on the pulsation profile, provide the electric stimulus to the vehicle occupant at the customized strength.

14. The method of claim 13, further comprising, based on feedback from the vehicle occupant, via the processor, adjusting a strength of the electric stimulus.

* * * * *